US008053464B2

(12) United States Patent
Quinn et al.

(10) Patent No.: US 8,053,464 B2
(45) Date of Patent: Nov. 8, 2011

(54) ATTRACTANTS FOR INSECTS SUCH AS FLIES

(75) Inventors: Brian P. Quinn, Alachua, FL (US); David A. Carlson, Gainesville, FL (US); Christopher J. Geden, Gainesville, FL (US); Ulrich R. Bernier, Gainesville, FL (US); Matthew M. Booth, Gainesville, FL (US); Jerome A. Hogsette, Jr., Gainesville, FL (US)

(73) Assignees: The United States of America as represented by the Secretary of Agriculture, Washington, DC (US); University of Florida Research Foundation Incorporated, Gainesville, FL (US)

( * ) Notice: Subject to any disclaimer, the term of this patent is extended or adjusted under 35 U.S.C. 154(b) by 887 days.

(21) Appl. No.: 12/044,213

(22) Filed: Mar. 7, 2008

(65) Prior Publication Data

US 2008/0234360 A1 Sep. 25, 2008

Related U.S. Application Data

(60) Provisional application No. 60/919,094, filed on Mar. 20, 2007.

(51) Int. Cl.
*A01N 43/36* (2006.01)
*A01P 19/00* (2006.01)
(52) U.S. Cl. ..................................................... 514/423
(58) Field of Classification Search ........................ None
See application file for complete search history.

(56) References Cited

U.S. PATENT DOCUMENTS

| 4,092,333 | A  | * | 5/1978 | Mookherjee et al. | ......... | 549/473 |
| 2004/0057977 | A1 | * | 3/2004 | Gardner et al. | ............... | 424/410 |
| 2005/0159599 | A1 |  | 7/2005 | Itoh et al. | | |

OTHER PUBLICATIONS

Pickens, L. et al., "Techniques for Trapping Flies on Dairy-Farms", *J. Agric. Entomol.*, vol. 4, (4), 1987, pp. 305-313.
Geden, C., "Methods for Monitoring Populations of House Flies; *Musca domestica* L. (*Diptera: Muscidae*)", *J. of Vector Ecology*, vol. 30, (2), 2005, pp. 1-7.
Pickens, L., et al., An Improved Bait for Flies (*Diptera: Muscidae, Calliphoridae*), *J. Med. Ent.*, vol. 10, (1), 1973, pp. 84-88.
Quinn, B., et al., "Analysis of Extracted and Volatile Components in Blackstrap Molasses Feed as Candidate House Fly Attractants", *J. of Chromatography A*, vol. 1139, 2007, pp. 279-284.
Howard, L.O., The House Fly—Disease Carrier; Fredrick A. Stokes, New York, NY, (1911), pp. 178-179.
M.S. Mulla, et al., Proceedings Paper of the 46th Annual Conference of California Mosquito Vector Control Assoc. (1978) pp. 70-73.

* cited by examiner

*Primary Examiner* — Shanon A Foley
(74) *Attorney, Agent, or Firm* — John D. Fado; G. Byron Stover; Gail E. Poulos

(57) ABSTRACT

A composition containing at least two members of the group consisting of propionic acid, benzoic acid, 2,6-dimethoxyphenol, 2-acetylpyrrole, 2-hydroxy-3-methyl-2-cyclopentanone, 2-methyltetrahydrofuran-3-one, and 3-methylbutanal; and water, and optionally a carrier or carrier material. The composition is useful for attracting insects (e.g., flies).
A method for attracting insects (e.g., flies) involving treating an object or area with an insect attracting effective amount of the composition described herein.

19 Claims, No Drawings

ATTRACTANTS FOR INSECTS SUCH AS FLIES

REFERENCE TO RELATED APPLICATION

This application claims the benefit of U.S. Provisional Application No. 60/919,094, filed 20 Mar. 2007, which is incorporated herein by reference in its entirety.

BACKGROUND OF THE INVENTION

The present invention relates to a composition containing at least two members of the group consisting of propionic acid, benzoic acid, 2,6-dimethoxyphenol, 2-acetylpyrrole, 2-hydroxy-3-methyl-2-cyclopentanone, 2-methyltetrahydrofuran-3-one, and 3-methylbutanal; and water, and optionally a carrier or carrier material. The composition is useful for attracting insects (e.g., flies). Furthermore, the present invention relates to a method for attracting insects (e.g., flies) involving treating an object or area with an insect attracting effective amount of the composition described herein.

House flies are pestiferous insects that are readily found on all continents except Antarctica. These insects are vectors for many diseases including shigellosis (Levine, O. S., and M. M. Levine, Rev. Inf. Dis., 13: 688-696 (1991)), enterohemorrhagic *Escherichia coli* O157:H7 (Moriya, K., et al., Med. Vet. Entomol., 13: 214-216 (1999); Iwasa, M., et al., J. Med. Entomol., 36: 109-112 (1999); Kobayashi, M., et al., Am. J. Trop. Med. Hyg., 61: 625-629 (1999); Sasaki, T., et al., J. Med. Entomol., 37: 945-949 (2000)), salmanellosis (Olsen, A. R., and T. S. Hammack, J. Food Protection., 63: 958-960 (2000); Mian, L. S., et al., J. Vector Ecol., 27: 82-85 (2002)), and cholera (Escheverria, P., et al., App. Environ. Microbiol., 46: 32-36 (1983); Fotedar, R., Acta-Tropica., 78: 31-34 (2001)).

Chemical insect attractants can be very powerful in luring insects to a particular location, and are widely used in insect traps, poison bait stations, and other killing devices. Foodstuffs are sometimes also used as insect attractants. For example, cured ham is used to attract yellowjackets of the *Vespula* species and rotting foodstuffs in water are used to attract flies. However, the rotting foodstuffs become highly offensive to humans.

Andersen, in U.S. Pat. No. 4,849,216, reported the use of poultry liver with a bacterial culture capable of breaking it down, plus a mixture of yeast and sugar as an attractant for flies in a water-based trap. However, the breakdown products are known to be very repulsive to humans. Harris, in U.S. Pat. No. 3,937,826, disclosed the use of two food ingredients together as a fly attractant, one being a granular fish food meat by-product, and the other a yellow sugar-based attractant. However, there is currently no single effective means of attracting flies and other flying insects using natural products which can be used to properly control flies without causing an offensive odor.

Therefore a need has been established for an active attractant to lure flying insects (e.g., flies) wherein the attractant causes little odor and is easy to handle (e.g., not sticky) but is fully effective at luring insects.

SUMMARY OF THE INVENTION

In accordance with the present invention there is provided a composition containing at least two members of the group consisting of propionic acid, benzoic acid, 2,6-dimethoxyphenol, 2-acetylpyrrole, 2-hydroxy-3-methyl-2-cyclopentanone, 2-methyltetrahydrofuran-3-one, and 3-methylbutanal; and water, and optionally a carrier or carrier material. The composition is useful for attracting insects (e.g., flies).

Also in accordance with the present invention there is provided a method for attracting insects (e.g., flies) involving treating an object or area with an insect attracting effective amount of the composition described herein.

DETAILED DESCRIPTION OF THE INVENTION

A composition is disclosed for attracting insects (e.g., flies), containing at least two members of the group consisting of propionic acid, benzoic acid, 2,6-dimethoxyphenol, 2-acetylpyrrole, 2-hydroxy-3-methyl-2-cyclopentanone, 2-methyltetrahydrofuran-3-one, and 3-methylbutanal; and water, and optionally a carrier or carrier material. 2-acetylpyrrole is also called 1-(1H-Pyrrol-2-yl)ethanone and 2-methyltetrahydrofuran-3-one is also called dihydro-2-methyl-3(2H)furanone.

Also disclosed is a method for attracting insects (e.g., flies) involving treating an object or area with an insect attracting effective amount of the composition described herein.

Generally, the composition contains the following: about 80 to about 800 mg (e.g. 80-800 mg) of propionic acid/ml; about 0.29 to about 2.9 mg (e.g., 0.29-2.9 mg) of benzoic acid/ml; about 0.35 to about 3.5 mg (e.g., 0.35-3.5 mg) of 2,6-dimethoxyphenol/ml; about 0.22 to about 2.2 mg (e.g., 0.22-2.2 mg) of 2-acetylpyrrole/ml; about 0.85 to about 8.5 mg (e.g., 0.85-8.5 mg) of 2-hydroxy-3-methyl-2-cyclopentanone/ml; about 0.48 to about 4.8 mg (e.g., 0.48-4.8 mg) of 2-methyltetrahydrofuran-3-one/ml; and about 0.55 to about 5.5 mg (e.g., 0.55-5.5 mg) of 3-methylbutanal/ml.

Generally the composition may be prepared by combining the following components some of which were dissolved in deionized (DI) water until saturation: propionic acid, 8 mL of a 800 mg/mL solution; benzoic acid, 6, mL of a water-saturated solution; 2,6-dimethoxyphenol, 3 mL of a water-saturated solution; 2-acetylpyrrole, 2 mL of a water-saturated solution; 2-hydroxy-3-methyl-2-cyclopentanone, 3 mL of a water-saturated solution; 2-methyltetrahydrofuran-3-one, 2.4 mg/mL water; and 3-methylbutanal, 3.25 mg/mL water.

This attractant blend composition is water-based to highlight the attractiveness of the chemical components listed above and also to eliminate any hazards posed by use of organic solvents. All compounds listed above that are labeled as water-saturated solution were prepared by adding excess amounts of solid compound into separate 50-mL volumetric flasks, filling the flasks to volume with DI water, and sonicating the solution for about 15 minutes. Each component was added to a beaker using a graduated pipette, except for 2-methyltetrahydrofuran-3-one and 3-methylbutanal which were added by Pasteur pipette. The blend was swirled to enhance mixing and poured into 20-mL scintillation vials until used in bioassays. No solvent besides water is required, preferably water is the sole solvent used. Organic solvent will inhibit or overwhelm the odor plume from the seven components due to extremely high concentration of the organic solvent as compared to the other components; furthermore, most solvents are flammable, which introduces a hazard to the manufacturer and user. Preferably organic solvents are not used.

The attractant composition of the present invention may be applied with a carrier component or carrier (e.g., biologically or agronomically acceptable carrier). The carrier component can be a liquid or a solid material. As is known in the art, the vehicle or carrier to be used refers to a substrate such as a membrane, hollow fiber, microcapsule, cigarette filter, gel, polymers, septa, or the like. All of these substrates have been used to release insect attractants in general and are well known in the art. Suitable carriers are well-known in the art and are selected in accordance with the ultimate application of interest. Solid carriers such as clays, cellulose-based and rubber materials and synthetic polymers may be used.

The amount of attractant used will be at least an effective amount. The term "effective amount," as used herein, means the minimum amount of attractant needed to attract the insects to a treated area or object when compared to the same area or object which is untreated. Of course, the precise amount needed will vary in accordance with the particular attractant composition used; the type of area or object to be treated; the number of days of attractiveness needed; and the environment in which the area or object is located. The precise amount of attractant can easily be determined by one skilled in the art given the teaching of this application. For example, one skilled in the art could follow the procedures utilized below; the attractant would be statistically significant in comparison to a negative control. The attractant composition may or may not contain a control agent for insects, such as a biological control agent or an insecticide known in the art to kill insects. Insect pheromones, such as (Z)-9-tricosene (muscalure), may also be included. Other compounds (e.g., insect attractants known in the art) may be added to the attractant composition provided they do not substantially interfere with the intended activity of the attractant composition; whether or not a compound interferes with attractant activity can be determined, for example, by the procedures utilized below.

A method is disclosed for attracting insects (e.g., flies) to an object (e.g., insect trap) or area involving treating (or exposing) the object or area with the above composition (optionally including the carrier material or carrier). The terms "object" or "area" as used herein include any place where the presence of target pests is not desirable, including any type of premises, which can be out-of-doors, such as in gardens, lawns, camping areas, and so forth, or indoors, such as in barns, garages, commercial buildings, homes, and so forth, or any area where pests are a problem.

The compositions can therefore be used for attracting harmful or troublesome insects such as blood-sucking and biting insects. The blood-sucking insects include biting flies (for example *Stomoxys calcitrans*), tsetse flies (*Glossina* species), horseflies (*Tabanus, Haematopota* and *Chrysops* species), house flies (for example *Musca domestica* and *Fannia canicularis*), meat flies (for example *Sarcophaga carnaria*), flies which cause myiasis (for example *Lucilia cuprina, Chrysomyia chloropyga, Hypoderma bovis, Hypoderma lineatum, Dermatobia hominis, Oestrus ovis, Gasterophilus intestinalis* and *Cochliomyia hominovorax*), and louse flies (for example *Melaphagus orinus*).

Unless defined otherwise, all technical and scientific terms used herein have the same meaning as commonly understood by one of ordinary skill in the art to which the invention belongs. Although any methods and materials similar or equivalent to those described herein can be used in the practice or testing of the present invention, the preferred methods and materials are now described.

The following examples are intended only to further illustrate the invention and are not intended to limit the scope of the invention as defined by the claims.

EXAMPLES

Outdoor cage studies: Outdoor cage studies were conducted in Coleman Insta-Clip® screen rooms (12 ft×14 ft×88 in) containing ca. 6000 flies (Musca domestica) that were 4-5 days old at the time of testing. Flies in the cages were provided with water and food (powdered milk, sugar, powdered egg). Food containers were removed from the cages 4-6 hours before tests were conducted.

In the first trial, 2-liter plastic containers with lids were used as assay containers. A 5-cm-diameter hole was cut in the lids of the containers. Two filter paper disks were placed in each container and the disks were treated with 2 ml of either de-ionized water or the 7-component blend of the present invention prepared by combining the following components some of which were dissolved in deionized (DI) water until saturation: propionic acid, 8 mL of a 800 mg/mL solution; benzoic acid, 6 mL of a water-saturated solution; 2,6-dimethoxyphenol, 3 mL of a water-saturated solution; 2-acetylpyrrole, 2 mL of a water-saturated solution; 2-hydroxy-3-methyl-2-cyclopentanone, 3 mL of a water-saturated solution; 2-methyltetrahydrofuran-3-one, 2.4 mg/mL water; and 3-methylbutanal, 3.25 mg/mL water. The containers (1 water, 1 blend) were placed in three cages. Counts of flies resting on the container lid were made 1, 3, and 5 minutes after introducing them into the cages. After 5 minutes, the hole in the container lid was sealed, the cages were removed, and flies collected in the containers were counted (Table 1)

In subsequent trials, Captivator® fly traps (Farnam Co.) were used as collection devices, and no instantaneous counts of resting flies were made. The traps were baited as before with two filter paper disks treated with 2 ml/trap of candidate attractants. In the first test using these traps, water controls were compared with the blend and with Farnam fly attractant (supposedly the best commercial attractant) which was diluted 1:30 following the manufacturer's guidelines. Traps were removed after 1 hour and the flies counted (Table 2). In the second jar trap study, the blend was compared with water controls and a 25% molasses solution (Table 3). In the third jar trap study, a four-way test was conducted comparing water controls, 25% molasses, Farnam fly attractant, and the 7-component blend (Table 4).

In a two-way choice test (Table 1), the 7-component blend was surprisingly 4 times more attractive than water controls within 1 minute of being deployed. After five minutes, the blend had surprisingly captured over 12 times as many flies as were collected in the water controls.

TABLE 1

Responses of house flies to 7-component blend and water control in outdoor cages

| Fly count/collection | Blend | Water control (std. error) |
|---|---|---|
| 1 min counts | 26.3 (5.1) | 6.7 (2.2) |
| 3 min counts | 21.5 (2.7) | 5.7 (1.6) |
| 5 min counts | 15.2 (2.6) | 6.3 (1.3) |
| Collection at 5 min | 69.5 (22.2) | 5.8 (3.9) |

"Counts" are visual counts of flies resting on the outside cover of the assay chamber at 1, 3 and 5 minutes after placement in the cages. At the end of 5 minutes, the entry port was sealed and the flies present in the assay chamber were counted.

In a three-way choice-test (Table 2), traps baited with the 7-component blend surprisingly captured over twice as many flies as molasses and six times as many flies as water controls.

TABLE 2

Collections of flies in outdoor cages using jar traps baited with water, 25% molasses (molasses diluted to 25% in deionized water (U.S. Pat. No. 6,966,142-Hogsette)), or 7-component blend.

| Rep | Water | 25% Mol. | Blend |
|---|---|---|---|
| 1 | 62 | 118 | 189 |
| 2 | 23 | 88 | 303 |
| 3 | 64 | 165 | 453 |
| Mean | 49.7 | 123.7 | 315.0 |

In a three-way choice test (Table 3), traps baited with the 7-component blend surprisingly captured over twice as many flies as the industry standard attractant (Farnam's product) and six times as many flies as water controls.

TABLE 3

Collections of flies in outdoor cages using jar traps baited with water, Farnam fly attractant (U.S. Pat. No. 5,008,107-Warner), or 7-component blend.

| | Water | Farnam | Blend |
|---|---|---|---|
| Tent 1 | 41 | 71 | 206 |
| Tent 2 | 30 | 121 | 235 |
| Tent 3 | 42 | 65 | 227 |
| Mean | 37.7 | 85.7 | 222.7 |

In a four-way choice situation (Table 4), traps baited with the 7-component blend surprisingly captured over twice as many flies as the industry standard attractant (Farnam's product), 1.5 times as many flies as molasses itself, and almost ten times as many flies as water controls.

TABLE 4

Collections of flies in outdoor cages using jar traps baited with water, 25% molasses (molasses diluted to 25% in deionized water (U.S. Pat. No. 6,966,142-Hogsette)), 7-component blend, or Farnam fly attractant (U.S. Pat. No. 5,008,107-Warner).

| Tent | Water | 25% Mol. | Blend | Farnam |
|---|---|---|---|---|
| 1 | 58 | 264 | 422 | 191 |
| 2 | 46 | 442 | 347 | 303 |
| 3 | 72 | 353 | 855 | 188 |
| Mean | 58.7 | 353.0 | 541.3 | 227.3 |

Dose response experiments with 7-component blend with flies of different ages: One-day-old flies were released into six outdoor screen rooms (ca. 3000 flies released/room), and food was removed from the rooms the night before the initial test. The following day, Captivator® traps baited with 3 ml of four candidate solutions were placed in each tent for one hour. Traps were baited with either water alone (control) or with the 7 component blend at 3, 10 or 100% using water as the diluent. At the end of the hour, traps were removed and the flies were sexed and counted. Food was placed in the screen rooms and the flies were allowed to feed ad libitum until they were five days old. By this time, females were visibly gravid and engorged with food. The food dishes were removed for one hour and traps baited as above were placed in the screen rooms a second time for a one-hour exposure.

Results: Surprisingly young, hungry females responded most strongly to a 10% dilution of the blend and a 3% dilution was about half as attractive as the 10% dilution (Table 5). The responses of young and hungry males were surprisingly similar to females; flies responded most strongly to a 10% dilution of the blend (Table 6). Response of older, fed, gravid females to the blend was weaker than was seen with young flies, but the response was surprisingly strongest to 3-10% dilutions (Table 7). Response of older, fed males to the blend was also weaker than was seen with young flies, surprisingly only the 10% dilution elicited a significant response by mature males (Table 8).

TABLE 5

Response of 2-day-old hungry female flies to 7-component blend at varying concentrations. Tests conducted in outdoor screen rooms using Captivator ® traps baited with 3 ml of candidate attractants pipetted onto 3 filter paper disks per trap.

| Concentration (% blend) | Mean (SE) flies caught |
|---|---|
| 0 (water) | 20.3 (2.6) c |
| 3 | 89.1 (13.1) b |
| 10 | 191.0 (30.9) a |
| 100 | 13.8 (2.1) c |
| ANOVA F | 23.86** |

**$P < 0.01$. Means followed by the same letter are not significantly different at $P = 0.05$.

TABLE 6

Response of 2-day-old hungry male flies to 7-component blend at varying concentrations. Tests conducted in outdoor screen rooms using Captivator ® traps baited with 3 ml of candidate attractants pipetted onto 3 filter paper disks per trap.

| Concentration (% blend) | Mean (SE) flies caught |
|---|---|
| 0 (water) | 10.3 (1.9) c |
| 3 | 49.2 (10.2) b |
| 10 | 81.1 (13.0) a |
| 100 | 7.1 (1.9) c |
| ANOVA F | 17.90** |

**$P < 0.01$. Means followed by the same letter are not significantly different at $P = 0.05$.

TABLE 7

Response of 5-day-old fed female flies to 7-component blend at varying concentrations. Tests conducted in outdoor screen rooms using Captivator ® traps baited with 3 ml of candidate attractants pipetted onto 3 filter paper disks per trap.

| Concentration (% blend) | Mean (SE) flies caught |
|---|---|
| 0 (water) | 4.3 (1.1) b |
| 3 | 32.0 (12.0) a |
| 10 | 26.8 (3.4) ab |
| 100 | 4.4 (1.4) b |
| ANOVA F | 5.32** |

**$P < 0.01$. Means followed by the same letter are not significantly different at $P = 0.05$.

TABLE 8

Response of 5-day-old fed male flies to 7-component blend at varying concentrations. Tests conducted in outdoor screen rooms using Captivator ® traps baited with 3 ml of candidate attractants pipetted onto 3 filter paper disks per trap.

| Concentration (% blend) | Mean (SE) flies caught |
|---|---|
| 0 (water) | 3.3 (1.0) b |
| 3 | 6.3 (2.1) b |
| 10 | 16.8 (3.4) a |

TABLE 8-continued

Response of 5-day-old fed male flies to 7-component blend at varying concentrations. Tests conducted in outdoor screen rooms using Captivator ® traps baited with 3 ml of candidate attractants pipetted onto 3 filter paper disks per trap.

| Concentration (% blend) | Mean (SE) flies caught |
|---|---|
| 100 | 0.6 (0.4) b |
| ANOVA F | 11.71** |

**$P < 0.01$. Means followed by the same letter are not significantly different at $P = 0.05$.

Evaluation of 7-versus 5-component blend in motel rooms: Five standard-size motel rooms were procured for this evaluation. Heaters in the room were set at 25° C. and the rooms were provisioned with water sources but not food. Five Captivator® traps were placed in each room, baited with 300 ml of the following: (1) 10% dilution of the 7-component blend; (2) 10% dilution of a 5-component blend (the original blend minus 2-hydroxy-3-methyl-2-cyclopentanone and 2-methyltetrahydrofuran-3-one); (3) water (negative control); (4) Farnam fly attractant, diluted 1:60 per manufacturer's instructions) (positive control—industry standard); and (5) 25% dilution of blackstrap molasses (positive control—natural product). Three thousand 2-day-old flies were released in each room with the traps. Two days later the traps were retrieved and the flies were counted (but not sexed).

Results: The 10% 5-component blend was surprisingly as attractive as the 7-component blend (Table 9).

TABLE 9

Response of 2-day-old flies (mixed sex) to 5- and 7-component blends, Farnam attractant, or 25% molasses. Tests conducted in hotel rooms with 3000 released flies using Captivator ® traps baited with 300 ml of candidate attractants per trap.

| Attractant | Mean (SE) flies caught |
|---|---|
| 7-component blend | 176.0 (39.2) cd |
| 5-component blend | 201.8 (34.4) c |
| Water control | 26.8 (4.0) d |
| Farnam attractant | 583.0 (32.0) b |
| 25% molasses | 866.2 (53.1) a |
| ANOVA F | 90.1** |

**$P < 0.01$. Means followed by the same letter are not significantly different at $P = 0.05$.

Dose-response test with 5-component blend in motel rooms: The motel rooms mentioned above were used for a second test under the same environmental conditions and using the same fly release rate. Five Captivator® traps were placed in each room, baited with 300 ml of the following: (1) 3% dilution of the 5-component blend; (2) 10% dilution of the 5-component blend (3) undiluted (100%) 5-component blend; (4) water (negative control); and (5) 25% dilution of blackstrap molasses (positive control). Traps were retrieved and the flies were counted three days later.

Results: The 10% dilution of the 5-component blend surprisingly collected significantly more flies than the higher concentrations or the water control (Table 10).

TABLE 10

Response of 2-day-old flies (mixed sex) to 5-component synthetic blend at varying dilutions in water, 25% molasses, or water. Tests conducted in hotel rooms with 3000 released flies using Captivator ® traps baited with 300 ml of candidate attractants per trap.

| Attractant | Mean (SE) flies caught |
|---|---|
| 10% 5-component blend | 489.2 (58.7) b |
| 25% 5-component blend | 110.2 (19.5) c |
| 100% 5-component blend | 50.8 (5.6) c |
| Water control | 63.8 (15.5)c |
| 25% molasses | 1140.0 (150.9) a |
| ANOVA F | 40.5** |

**$P < 0.01$. Means followed by the same Letter are not significantly different at $P = 0.05$.

Conclusions: A 7-component synthetic attractant blend for house flies was developed. In outdoor screen house trials using small amounts of attractant (3 ml), this blend was found to at least as attractive as molasses or the most popular commercial fly attractant (Farnam Fly Attractant). Dose-response trials conducted in outdoor screen houses with 3 ml of attractant demonstrated that the blend could be diluted at least 10-fold in water with no diminution of efficacy. Follow-up studies conducted in empty motel rooms using a larger volume of attractant (300 ml) demonstrated that the two most costly chemicals could be eliminated from the blend with no loss of attractiveness. Dose-response trials conducted in motel rooms with 300 ml of this 5-component blend confirmed that a 10-fold dilution of the attractant in water was at least as attractive as solutions prepared at higher concentrations.

All of the references cited herein, including U.S. patents, are incorporated by reference in their entirety. Also incorporated by reference in their entirety are the following: Akochi-K, E., et al., J. Agric. Food Chem., 45: 3368-3373 (1997); Alissandrakis, E., et al., J. Sci. Food Agric., 85: 91-97 (2005); Binkley, W. W., and M. L. Wolfrom, Adv. Carbohyd. Chem., 3: 1-24 (1953); Brown, A. W. A., et al., J. Econ. Entomol., 54: 670-674 (1961); Carlson, D. A., et al., Science., 174: 76-78 (1971); Carlson, D. A., and M. Beroza, Environ. Entomol., 2: 555-559 (1973); Cosse, A. A., and T. C. Baker, J. Agric. Entomol., 13: 301-317 (1996); Counet, C., et al., J. Agric. Food Chem., 50: 2385-2391 (2002); de Brito, E. S., et al., J. Sci. Food Agric., 82: 534-537 (2002); Dierssen, G. A., et al., Int. Sugar J., 58: 35-39 (1956); El-Sayed, A. M., et al., J. Agric. Food Chem., 53: 953-958 (2005); Escheverria, P., et al., App. Environ. Microbiol., 46: 32-36 (1983); Fotedar, R., Acta-Tropica., 78: 31-34 (2001); Frishman, A. M., and J. G. Matthysse, Agricultural Experimentation Memo No. 394, Cornell University, Ithaca, N.Y., 1966, pp. 21-89; Garrett, D. A., Ph.D. Thesis, Oklahoma State University, Stillwater, Okla., 1965, pp. 43-67; Geden, C. J., J. Vector Ecol., 30:1-7 (2005); Godshall, M. A., et al., J. Agric. Food Chem., 28: 856-858 (1980); Hashim, P., et al, J. Sci. Food. Agric., 79: 987-994 (1999); Hashizume, T., et al., Agric. Biol. Chem., 31: 324-329 (1967); Howard, L. O., The House Fly—Disease Carrier, Fredrick A. Stokes, New York, N.Y., (1911); Iwasa, M., et al., J. Med. Entomol., 36: 109-112 (1999); Johnson, R. R., et al., J. Agric. Food Chem., 17: 22-24 (1969); Kobayashi, M., et al., Am. J. Trop. Med. Hyg., 61: 625-629 (1999); Leunissen, M., et al., J. Agric. Food Chem., 44: 2694-2699 (1996); Levine, O. S., and M. M. Levine, Rev. Inf. Dis., 13: 688-696 (1991); Mayer, M. S., USDA Agricultural Handbook 403 (1971) pages 23-26; Meade, G. P., and J. C. P. Chen, in G. P. Meade, J. C. P. Chen (Editors), Cane Sugar Handbook, Wiley, New York, N.Y., 10th ed., 1977, pp. 43-47; Mian, L. S., et al., J. Vector Ecol., 27: 82-85 (2002); Moriya, K., et al., Med. Vet. Entomol., 13: 214-216 (1999); Mulla, M. S., et al., J. Econ. Entomol., 70: 644-648 (1977); Mulla, M. S., et al., Proceedings Paper of the 46th Annual Conference of California Mosquito Vector Control Assoc. (1978), pages 60-73; Olsen, A. R., and T. S. Hammack, J. Food Protection., 63: 958-960 (2000); Pickens, L. G., et al., J. Med. Entomol., 10: 84-88 (1973); Pickens, L. G., and R. W. Miller, J. Agric. Entomol., 4: 305-313 (1987); Quinn, B. P., et al., J. of Chromatography A, 1139: 279-284 (2007); Robacker, D. C., and R. J. Bartlet, J. Chem. Ecol., 23: 2897-2915 (1997); Sasaki, T., et al., J. Med. Entomol., 37: 945-949 (2000); Schwab, W., J. Agric. Food Chem., 46: 2266-2269 (1998); Tokitomo, Y., et al., Agric. Biol. Chem., 48: 2869-2870 (1984); Wein, M., et al., J. Agric. Food Chem., 49: 2427-2432 (2001); Willson, H. R., and M. S. Mulla, Environ. Entomol., 2: 815-822 (1973); Yokota, M., and I. S. Fagerson, J. Food Sci., 26: 1091-1094 (1971). Also incorporated by reference in their entirety are the following U.S. Pat. Nos. 6,966,142; 5,008,107; 4,849,216. Also incorporated by reference in its entirety is U.S. Patent Application Publication 2005/0142160.

Thus, in view of the above, the present invention concerns (in part) the following:

A composition (for attracting insects (e.g., flies)), comprising (or consisting essentially of or consisting of) at least two members of the group consisting of propionic acid, benzoic acid, 2,6-dimethoxyphenol, 2-acetylpyrrole, 2-hydroxy-3-methyl-2-cyclopentanone, 2-methyltetrahydrofuran-3-one, and 3-methylbutanal; and water, and optionally a carrier or carrier material.

The above composition, wherein said composition contains at least three members of the group consisting of propionic acid, benzoic acid, 2,6-dimethoxyphenol, 2-acetylpyrrole, 2-hydroxy-3-methyl-2-cyclopentanone, 2-methyltetrahydrofuran-3-one; and 3-methylbutanal; and water, and optionally a carrier or carrier material.

The above composition, wherein said composition contains at least four members of the group consisting of propionic acid, benzoic acid, 2,6-dimethoxyphenol, 2-acetylpyrrole, 2-hydroxy-3-methyl-2-cyclopentanone, 2-methyltetrahydrofuran-3-one, and 3-methylbutanal; and water, and optionally a carrier or carrier material.

The above composition, wherein said composition contains at least five members of the group consisting of propionic acid, benzoic acid, 2,6-dimethoxyphenol, 2-acetylpyrrole, 2-hydroxy-3-methyl-2-cyclopentanone, 2-methyltetrahydrofuran-3-one, and 3-methylbutanal; and water, and optionally a carrier or carrier material.

The above composition, wherein said composition contains at least six members of the group consisting of propionic acid, benzoic acid, 2,6-dimethoxyphenol, 2-acetylpyrrole, 2-hydroxy-3-methyl-2-cyclopentanone, 2-methyltetrahydrofuran-3-one, and 3-methylbutanal; and water, and optionally a carrier or carrier material.

The above composition, wherein said composition contains propionic acid, benzoic acid, 2,6-dimethoxyphenol, 2-acetylpyrrole, 2-hydroxy-3-methyl-2-cyclopentanone, 2-methyltetrahydrofuran-3-one, and 3-methylbutanal; and water, and optionally a carrier or carrier material.

The above composition, wherein said composition does not contain propionic acid.

The above composition, wherein said composition does not contain benzoic acid.

The above composition, wherein said composition does not contain 2,6-dimethoxyphenol.

The above composition, wherein said composition does not contain 2-acetylpyrrole.

The above composition, wherein said composition does not contain 2-hydroxy-3-methyl-2-cyclopentanone.

The above composition, wherein said composition does not contain 2-methyltetrahydrofuran-3-one.

The above composition, wherein said composition does not contain 3-methylbutanal.

The above composition, wherein said composition optionally contains at least one insect pheromone. The above composition wherein said insect pheromone is (Z)-9-tricosene.

The above composition, wherein said composition optionally contains at least one insecticide.

The above composition, wherein said composition optionally contains at least one insect attractant.

The above composition, wherein said composition does not contain sugars found in molasses (e.g., sucrose, fructose, glucose).

The above composition, wherein said composition contains water, about 80 to about 800 mg of propionic acid/ml, about 0.29 to about 2.9 mg of benzoic acid/ml, about 0.35 to about 3.5 mg of 2,6-dimethoxyphenol/ml, about 0.22 to about 2.2 mg of 2-acetylpyrrole/ml, about 0.85 to about 8.5 mg of 2-hydroxy-3-methyl-2-cyclopentanone/ml, about 0.48 to about 4.8 mg of 2-methyltetrahydrofuran-3-one/ml, and about 0.55 to about 5.5 mg of 3-methylbutanal/ml.

The above composition, wherein said composition consists essentially of (or consists of) propionic acid, benzoic acid, 2,6-dimethoxyphenol, 2-acetylpyrrole, 2-hydroxy-3-methyl-2-cyclopentanone, 2-methyltetrahydrofuran-3-one, 3-methylbutanal, water, optionally a carrier or carrier material, optionally at least one insect pheromone, optionally at least one insecticide, and optionally at least one insect attractant.

The above composition, wherein said composition contains water, about 80 to about 800 mg of propionic acid/ml, about 0.29 to about 2.9 mg of benzoic acid/ml, about 0.35 to about 3.5 mg of 2,6-dimethoxyphenol/ml, about 0.22 to about 2.2 mg of 2-acetylpyrrole/ml, and about 0.55 to about 5.5 mg of 3-methylbutanal/ml.

The above composition, wherein said composition consists essentially of (or consists of) propionic acid, benzoic acid, 2,6-dimethoxyphenol, 2-acetylpyrrole, 3-methylbutanal, water, optionally a carrier or carrier material, optionally at least one insect pheromone, optionally at least one insecticide, and optionally at least one insect attractant.

A method for attracting insects (e.g., flies), comprising (or consisting essentially of or consisting of) exposing to the atmosphere an insect attracting effective amount of the above composition.

The above method, wherein said insects are selected from the group consisting of *Musca domestica*, *Fannia canicularis*, and mixtures thereof. The above method wherein said insects are *Musca domestica*.

Other embodiments of the invention will be apparent to those skilled in the art from a consideration of this specification or practice of the invention disclosed herein. It is intended that the specification and examples be considered as exemplary only, with the true scope and spirit of the invention being indicated by the following claims.

We claim:

1. A composition comprising at least five members of the group consisting of propionic acid, benzoic acid, 2,6-dimethoxyphenol, 2-acetylpyrrole, 2-hydroxy-3-methyl-2-cyclopentanone, 2-methyltetrahydrofuran-3-one, 3-methylbutanal, and mixtures thereof, and water, and optionally a carrier or carrier material.

2. The composition according to claim 1, wherein said composition contains about 80 to about 800 mg of propionic acid/ml, about 0.29 to about 2.9 mg of benzoic acid/ml, about 0.35 to about 3.5 mg of 2,6-dimethoxyphenol/ml, about 0.22 to about 2.2 mg of 2-acetylpyrrole/ml, about 0.85 to about 8.5 mg of 2-hydroxy-3-methyl-2-cyclopentanone/ml, about 0.48 to about 4.8 mg of 2-methyltetrahydrofuran-3-one/ml, and about 0.55 to about 5.5 mg of 3-methylbutanal/ml.

3. The composition according to claim 1, wherein said composition optionally contains at least one insect pheromone.

4. The composition according to claim 3, wherein said insect pheromone is (Z)-9-tricosene.

5. The composition according to claim 1, wherein said composition optionally contains at least one insecticide.

6. The composition according to claim 1, wherein said composition optionally contains at least one insect attractant.

7. The composition according to claim 1, wherein said composition does not contain 2-hydroxy-3-methyl-2-cyclopentanone.

8. The composition according to claim 1, wherein said composition does not contain 2-methyltetrahydrofuran-3-one.

9. The composition according to claim 1, wherein said composition contains about 80 to about 800 mg of propionic acid/ml, about 0.29 to about 2.9 mg of benzoic acid/ml, about 0.35 to about 3.5 mg of 2,6-dimethoxyphenol/ml, about 0.22 to about 2.2 mg of 2-acetylpyrrole/ml, and about 0.55 to about 5.5 mg of 3-methylbutanal/ml.

10. The composition according to claim 1, wherein said composition consists essentially of propionic acid, benzoic acid, 2,6-dimethoxyphenol, 2-acetylpyrrole, 3-methylbutanal, water, optionally a carrier or carrier material, optionally at least one insect pheromone, optionally at least one insecticide, and optionally at least one insect attractant.

11. The composition according to claim 1, wherein said composition consists essentially of propionic acid, benzoic acid, 2,6-dimethoxyphenol, 2-acetylpyrrole, 2-hydroxy-3-methyl-2-cyclopentanone, 2-methyltetrahydrofuran-3-one, 3-methylbutanal, water, optionally a carrier or carrier material, optionally at least one insect pheromone, optionally at least one insecticide, and optionally at least one insect attractant.

12. A method for attracting insects, said method involving treating an object or area with an insect attracting effective amount of the composition according to claim 1.

13. The method according to claim 12, wherein said insects are selected from the group consisting of *Musca domestica, Fannia canicularis*, and mixtures thereof.

14. The method according to claim 12, wherein said insects are *Musca domestica*.

15. The composition according to claim 1, wherein said composition contains propionic acid, benzoic acid, 2,6-dimethoxyphenol, 2-acetylpyrrole, and 3-methylbutanal.

16. The composition according to claim 1, wherein said composition contains propionic acid, benzoic acid, 2,6-dimethoxyphenol, 2-acetylpyrrole, 2-hydroxy-3-methyl-2-cyclopentanone, 2-methyltetrahydrofuran-3-one, and 3-methylbutanal.

17. The composition according to claim 1, wherein said composition consists of propionic acid, benzoic acid, 2,6-dimethoxyphenol, 2-acetylpyrrole, 3-methylbutanal, water, optionally a carrier or carrier material, optionally at least one insect pheromone, optionally at least one insecticide, and optionally at least one insect attractant.

18. The composition according to claim 1, wherein said composition consists of propionic acid, benzoic acid, 2,6-dimethoxyphenol, 2-acetylpyrrole, 2-hydroxy-3-methyl-2-cyclopentanone, 2-methyltetrahydrofuran-3-one, 3-methylbutanal, water, optionally a carrier or carrier material, optionally at least one insect pheromone, optionally at least one insecticide, and optionally at least one insect attractant.

19. A composition consisting of propionic acid, benzoic acid, 2,6-dimethoxyphenol, 2-acetylpyrrole, 3-methylbutanal, water, optionally a carrier or carrier material, optionally at least one insect pheromone, optionally at least one insecticide, and optionally at least one insect attractant.

* * * * *